United States Patent [19]
Gardner et al.

[11] 3,939,183
[45] Feb. 17, 1976

[54] PURIFICATION OF MALEIC ANHYDRIDE

[75] Inventors: John D. Gardner, Richmond; John F. Manning, Albany, both of Calif.

[73] Assignee: Chevron Research Company, San Francisco, Calif.

[22] Filed: Oct. 5, 1973

[21] Appl. No.: 404,076

[52] U.S. Cl. .................... 260/346.8 M; 260/346.7
[51] Int. Cl.² ..................................... C07D 307/60
[58] Field of Search .................. 260/346.8 M, 346.7

[56] References Cited
UNITED STATES PATENTS

| | | | |
|---|---|---|---|
| 2,296,218 | 9/1942 | Middleton, Jr. | 260/346.8 |
| 3,586,703 | 6/1971 | Martinez et al. | 260/346.8 |

*Primary Examiner*—Natalie Trousof
*Assistant Examiner*—Bernard I. Dentz
*Attorney, Agent, or Firm*—G. F. Magdeburger; John Stoner, Jr.; T. G. De Jonghe

[57] ABSTRACT

A method for obtaining purified polycarboxylic anhydrides of good color stability which comprises combining and contacting a metal halide and $P_2O_5$ or a perborate with the crude anhydride before final distillation of the crude anhydride. Preferred metal halides are alkaline earth and transition metal halides, with magnesium, calcium and iron chlorides being particularly preferred. The method is especially advantageously applied to maleic anhydride purification, especially maleic anhydride produced by butane oxidation.

9 Claims, 1 Drawing Figure

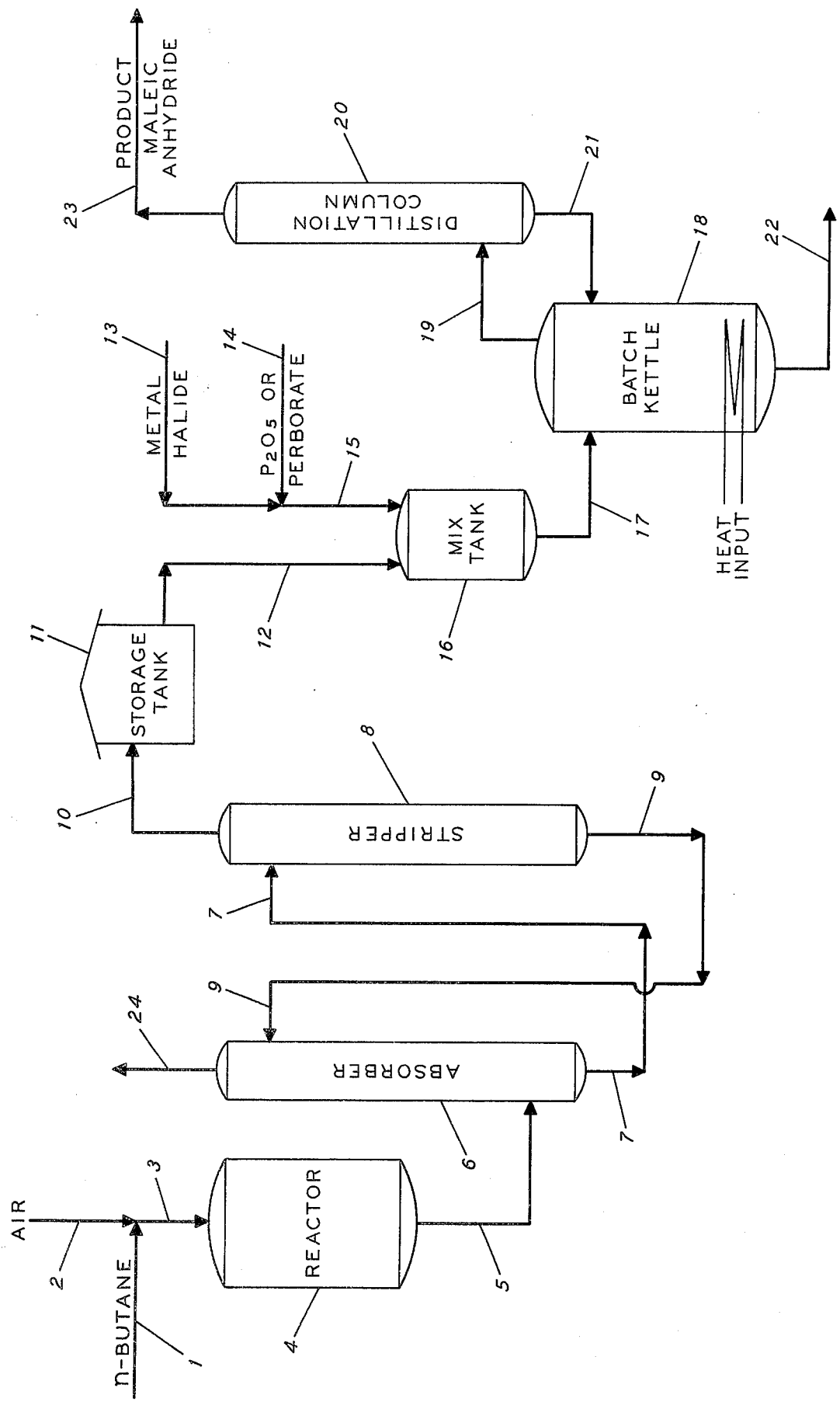

PURIFICATION OF MALEIC ANHYDRIDE

BACKGROUND OF THE INVENTION

The present invention relates to purification of polycarboxylic anhydrides such as phthalic anhydride and maleic anhydride, and especially maleic anhydride. More particularly, the present invention relates to obtaining anhydride products, especially a maleic anhydride product, of good color stability.

Polycarboxylic anhydrides such as phthalic anhydride and maleic anhydride are commercially produced by oxidation of a hydrocarbon feedstock using a catalyst to obtain specificity for the reaction. Typical feedstocks for phthalic anhydride production include naphthalene and orthoxylene. Maleic anhydride can be produced from a number of different hydrocarbon feedstocks, including benzene, butane, butene, furfural, and crotonaldehyde. Catalysts for both processes usually contain the oxides of vanadium, along with the oxides of other elements as modifiers.

Production of phthalic anhydride or maleic anhydride includes means to recover the anhydride from the oxidation reactor effluent, for example by absorption of the anhydride followed by stripping the anhydride from the absorbent to obtain a crude anhydride stream, and means to purify the recovered crude anhydride, for example by distillation to obtain product anhydride. One of the important specifications for the purified product anhydride is color stability. The color of phthalic anhydride or maleic anhydride is commonly measured by so-called APHA color standards using standard platinum-cobalt solutions prepared in accordance with ASTM D-2280-66 procedure. This color scale was developed by the American Public Health Association and is also known as the Hazen Platinum Cobalt Scale. A description may be found at page 2048 of the 5th edition of "Standard Methods of Chemical Analysis", by Wilford W. Scott.

Typical specifications on product maleic anhydride call for an APHA or Hazen color of 20 or lower for molten anhydride and a color of 40 or less after 2 hours heating at 140°C. Good commercial maleic anhydride has a Hazen color below 125 after 24 hours at 140°C. Because the color of maleic anhydride is particularly prone to degrade (become darker) upon heating and because color tests frequently call for measurement after a prolonged period of heating, the color stability of maleic anhydride is also frequently referred to as color thermal stability.

Various methods have been employed to obtain colorstable carboxylic acid anhydrides. For example, U.S. Pat. No. 2,129,166 discloses color-stability improvement by heating crude maleic anhydride for a considerable length of time and then distilling to obtain a product anhydride; U.S. Pat. No. 2,134,531 discloses the use of sulfuric acid to treat crude maleic anhydride followed by distillation to obtain a product maleic anhydride; U.S. Pat. No. 2,150,331 discloses the formation of a maleic anhydride compound with anthracene followed by separation of the anthracenemaleic anhydride compound and then decomposing the compound to obtain pure maleic anhydride vapor; U.S. Pat. No. 2,296,218 discloses heating crude maleic anhydride with a metal compound selected from the oxides and hydroxides of sodium, potassium, lithium, calcium, zinc and magnesium and the halides of zinc, iron and aluminum and then distilling the treated maleic anhydride to recover a product maleic anhydride; U.S. Pat. No. 2,308,588 discloses heating crude maleic anhydride with an oxide of boron and then distilling to obtain purified maleic anhydride; U.S. Pat. No. 2,831,896 teaches that alkali metal cations cause undesirable decarboxylation of maleic anhydride, especially above 150°C, and that therefore if an alkali metal cation is inadvertently present a boron compound should be added before the crude maleic anhydride is distilled; U.S. Pat. No. 2,959,600 discloses adding paraldehyde to crude maleic anhydride, heating and then distilling to obtain purified maleic anhydride. British Pat. No. 1,204,846 and U.S. Pat. No. 3,564,022 disclose a process comprising "treating crude maleic anhydride at a temperature of from about 130°C. up to but not exceeding the boiling point of the maleic anhydride with a small amount of a heat stable acidic compound or mixture thereof, such as, the inorganic acids such as ortho phosphoric, meta phosphoric, pyrophosphoric, phosphorus, the oxides of phosphorus and sulfur such as $P_2O_3$, $P_2O_4$, $P_2O_5$ and $SO_3$; the strong organic acids such as the alkane, aromatic, xylene and naphthalene sulfonic acids and the trichloro-, dichloro-acetic acids, oxalic acid, fumaric acid, the Lewis acids such as aluminum chloride, zinc chloride, stannic chloride and ferric chloride. The molten mass is thereafter distilled at a pressure of from about 100 to about 760 mm. Hg and a small amount of the stabilizer [organic sulfide compound] is added to the treated and distilled product yielding a maleic anhydride composition displaying the aforesaid storage color stability."

Note that in this disclosed process the maleic anhydride is first treated with a Lewis acid, and after this treatment and distillation an organic sulfide stabilizer is required for stability.

U.S. Pat. No. 3,586,703 discloses the addition of alkali and alkaline earth sulfates and halides to product commercial maleic anhydride in order to stabilize the color of maleic anhydride; U.S. Pat. No. 3,041,251 discloses heating crude maleic anhydride with sodium perborate ($NaBO_3$) and distilling off the purified maleic anhydride; U.S. Pat. No. 3,115,477 discloses improving the color stability of maleic anhydride by: (1) treating crude maleic anhydride with from 0.1 to 10% of phosphorus pentoxide at a temperature of about 140° to 200°C.; (2) distilling maleic anhydride therefrom; and (3) adding color-stabilizing amounts of thiodipropionic acid or esters thereof to the distilled maleic anhydride. U.S. Pat. No. 3,622,600 discloses preparation of color-stable maleic anhydride by passing molten maleic anhydride through a bed of alkali sulfates or halides; and U.S. Pat. No. 3,636,057 discloses improving the color stability of maleic anhydride by adding trace amounts — that is, 50 to 2,000 ppm — of a hydrocarbyl thiophosphate to maleic anhydride.

From the above it can be seen that a very wide range of methods have been disclosed for improving the color stability of carboxylic acid anhydrides such as maleic anhydride. The use of metal halides for purification and enhancement of color stability has been disclosed, and it can also be seen by reviewing the long list that $P_2O_5$ has been disclosed for enhancing the color stability. The use of these two specific agents together has not been disclosed nor has the use of sodium perborate with metal halides been disclosed for color stability enhancement, and U.S. Pat. No. 2,296,218 teaches that nothing is needed in addition to the use of a metal halide to obtain an essentially unchanging color — that is, very high color stability for a product maleic anhydride.

SUMMARY OF THE INVENTION

According to the present invention an improvement is made in a process for obtaining purified phthalic anhydride or maleic anhydride from crude anhydride by steps comprising heating the crude anhydride in the presence of a treating agent, distilling the crude anhydride, and withdrawing a purified anhydride overhead as a distilled product. The improvement comprises combining, contacting, and heating a metal halide and $P_2O_5$ or an alkali or alkaline earth perborate with the crude anhydride before distilling the crude anhydride to obtain rerun product anhydride.

The above improvement results in obtaining purified anhydrides, especially maleic anhydride, of high color stability. The reference to color stability herein is with respect to color stability upon standing (storage) and stability upon heating at an elevated temperature for a period of time.

Preferably the metal halide is an alkaline earth or transition metal halide. Of the halides, chloride is most preferred, and of the metals, magnesium, calcium, strontium, barium, manganese, vanadium and iron are especially preferred.

Among other factors, the present invention is based on our finding that the use of $P_2O_5$ or a perborate and metal halides such as magnesium chloride results in markedly improving the color stability of a carboxylic acid anhydride, especially maleic anhydride, and also is based on a large number of experimental runs which indicate that this marked or very large improvement in color stability is quite superior to the improvement achieved from any of a large number of other methods which we tried. We have found that particularly preferred halides for use in the process of the present invention are magnesium, calcium, manganese and iron halides. Of the above metal halides magnesium, calcium, and iron (especially $Fe^{+3}$) are the most preferred.

Usual amounts of the metal halides and $P_2O_5$ or perborate range from 0.01 to 2 weight percent each based on the crude anhydride. Preferred amounts of the metal halides and $P_2O_5$ or perborate are from about 0.1 to 1.0 weight percent each based on the crude maleic anhydride or other carboxylic acid anhydride treated in accordance with the present invention. Preferred perborates are alkali, especially Na, K or Rb, and alkaline earth, especially Mg, Ca and Ba, perborates. Sodium perborate is particularly preferred for use in the process of the present invention.

Treating times with the metal halide and $P_2O_5$ or perborate preferably range from 0.1 to 12 hours, more preferably 0.5 to 2 hours, in duration. Treating temperatures range from 130° to 500°F., preferably 250° to 350°F.

The terminology "crude anhydride" or "crude maleic anhydride" is used herein to mean the anhydride before final distillation to obtain the product or finished anhydride. The crude anhydride is usually more than 95% pure anhydride.

We have found that the present invention is especially advantageously applied to crude maleic anhydride produced by oxidation of normal butane using a catalyst comprising vanadium and phosphorus oxides such as the catalyst described in commonly assigned application Ser. No. 263,883, filed June 19, 1972 and now abandoned, particularly when the crude maleic anhydride is separated from the effluent from the n-butane oxidation step using an organic absorbent. Typical absorbents include dibutylphthalate, dihexylphthalate, dodecenyl succinic anhydride, etc. Thus, in accordance with a preferred embodiment of the present envention, a process is provided for obtaining purified maleic anhydride from crude maleic anhydride produced by steps comprising oxidizing butane over a particulate solid catalyst comprising vanadium and phosphorus oxides to obtain a gaseous effluent containing maleic anhydride, contacting the gaseous effluent with an organic absorbent, thereby absorbing maleic anhydride and obtaining a maleic-anhydride-rich absorbent, stripping maleic anhydride from the rich absorbent to obtain crude maleic anhydride, which process comprises a. combining and contacting 0.05 to 2 weight percent Mg, Ca, Mn, or Fe chloride and 0.05 to 1 weight percent $P_2O_5$ with the crude maleic anhydride to obtain a mixture, b. holding the mixture at a temperature between about 250° and 350°F. for between 0.1 and 12 hours, and c. distilling the mixture to obtain a purified overhead maleic anhydride fraction.

In an even more preferred process, the crude maleic anhydride is topped prior to adding the treating agents.

BRIEF DESCRIPTION OF THE DRAWING

The drawing is a schematic process flow diagram illustrating a preferred embodiment of the present invention wherein a maleic anhydride product is produced.

FURTHER DESCRIPTION OF THE DRAWING

Referring now in more detail to the drawing, normal butane feed via line 1 and air via line 2 are introduced via line 3 to reactor 4. In reactor 4 the butane is oxidized to obtain maleic anhydride. The effluent is withdrawn from the reactor via line 5 and fed to absorber 6. In absorber 6 the effluent gaseous stream containing maleic anhydride is contacted with a liquid organic absorbent flowing downwardly countercurrent to the gaseous reactor effluent. Maleic anhydride is absorbed into the absorbent and the unabsorbed gases such as nitrogen, etc., are removed via line 24 from the top of the absorber. The maleic-anhydride-rich absorbent is removed from the bottom of the absorber via line 7 and fed to stripper 8 wherein maleic anhydride is distilled out of the absorbent. The stripped absorbent is removed via line 9 at the bottom of the stripper and recycled to the top of the absorber for reuse. The crude maleic anhydride, usually of about 99% purity or greater, is removed from the stripper via line 10. The crude maleic anhydride is stored in storage tank 11 so that it can be processed batchwise in quantities as desired.

Treatment of the crude maleic anhydride may be accomplished by mixing the treating agents in a small portion of crude maleic anhydride, and then charging this portion along with the remainder of the batch to a batch-treating kettle.

Thus, as described, a portion of a batch is withdrawn from storage tank 11 via line 12 and is mixed with a metal halide added via lines 13 and 15 and $P_2O_5$ or perborate added via lines 14 and 15 to mix tank 16 in accordance with the present invention. The size batch as desired is passed from mix tank 16 into batch kettle 18 via line 17, along with additional crude maleic anhydride from tank 11 via lines 12 and 17. The batch contains $P_2O_5$ or perborate and a metal halide such as magnesium chloride mixed into at least a portion of the total batch in mix tank 16 before the total batch is introduced to batch kettle 18. Various other means can be employed to introduce the metal halide and the $P_2O_5$ or perborate into the maleic anhydride before the maleic anhydride is distilled. For example, the total batch of crude maleic anhydride and the treating agents can be added directly to tank 18. Also, the process can be made continuous. In any case, in the process of the present invention the metal halide plus $P_2O_5$ or perborate is introduced to the crude anhydride prior to the final distillation step. Treatment may be accomplished in a sequential manner, i.e., the crude maleic anhydride may be mixed and heated with $P_2O_5$ prior to adding the metal halide, or in a simultaneous manner, i.e., the two agents may be added together.

The mixture, as indicated in the preferred embodiment of the drawing, is heated in batch kettle 18 at a temperature preferably between 150° and 350°F. Preferred heating temperatures in batch kettle 18 are between about 250° and 325°F., and preferred cooling time in the kettle is 10 minutes to 24 hours, more preferably ½ to 12 hours.

Heat input to batch kettle 18 is indicated schematically by heat input means 25. It is to be understood that the drawing is only schematic and many common features are omitted such as heating means for stripper 8 and cooling means for distillation column 20, and various ancillary expected processing steps.

After the treating step is completed, batch kettle 18 becomes a distillation pot for column 20. Vaporous crude maleic anhydride is withdrawn from batch kettle 18 via line 19 and fed to distillation column 20. During distillation, the condensed maleic anhydride and any heavy ends are returned to the batch kettle via line 21. At the completion of one or more batch distillations, the bottoms material is withdrawn via line 22 from the batch kettle. Steam or hot water may be used to aid in bottoms removal from the batch kettle. The overhead from distillation column 20 usually is taken in at least two fractions, including a top cut or forecut, which is recycled to the over-all process, and after the forecut a product cut, which is the purified maleic anhydride of enhanced color stability.

EXAMPLES

In all of the following examples, maleic anhydride was produced by oxidizing n-butane using a catalyst and process as described in the aforesaid Ser. No. 263,883 which is now abandoned, and maleic anhydride was recovered from the effluent using an organic absorbent.

Example 1

In this example, crude maleic anhydride was continuously recovered from a dihexylphthalate organic absorbent solution by distilling through a 10-sieve-tray column at a reboiler temperature of 217°C. under an average pressure of 50 torr. Under these conditions, maleic anhydride came overhead at a temperature in the range of 235° to 239°F. This crude anhydride (27.5 kg) was then charged to a 20-sieve-tray distillation column, and 1376 g of maleic anhydride was taken overhead at a 9:1 reflux ratio.

To the bottoms from the above distillation, $P_2O_5$ was added in the amount of 510 g (0.2%) (unless otherwise indicated, percentages are by weight). The resulting mixture was heated at 300°F. for 6 hours and was then filtered. A portion of the filtrate (5125 g) was mixed with 10 g (0.2%) of magnesium chloride and heated for 1 hour at 243°F. Following this, the treated maleic anhydride was distilled through a 2.5 inch × 3 foot Penn State packed column at a pressure of 57 torr. Under these conditions, 94% of the charge was taken overhead in 10 fractions at a boiling point of 394.4°–395.5°F.

Each fraction was tested as to color thermal stability by charging 50 ml of molten maleic anhydride to a large test tube and comparing the color of this stock to an equal depth of Hazen color standard. The tubes containing each fraction were covered and placed in an oven at 140°F. Colors after 3 hours were from 5 to 10 Hazen and after 24 hours from 15 to 35 Hazen. Samples of commercial maleic anhydride from various manufacturers tested under the same conditions had 24-hour colors of 30 to 175 Hazen.

This example illustrates the excellent maleic-anhydride color thermal stability obtained by the process of the present invention.

Example 2

Crude maleic anhydride recovered by distilling from an organic absorbent (1724 g) was charged to a 20-sieve-tray column. A total of 84 g was distilled overhead at 238°F. under a pressure of 51 torr.

A fraction of the bottoms (1604 g) was mixed with 3.2 g (0.2%) $P_2O_5$ and heated with stirring for 5 hours at 310°F. At the end of this time, 1.6 g (0.1%) of magnesium chloride was added, and the resulting mixture was distilled in a 20-sieve-tray column under a pressure of 50 torr. A forerun fraction — 100 g (6% of charge) — and a product fraction — 1206 g (75% of charge) — were taken overhead. These two fractions after 24 hours at 140°C. had colors of 60 and 15 Hazen, respectively.

This example illustrates the process of the present invention utilizing a smaller magnesium chloride dosage and indicates flexibility in the time at which the metal halide is added in the treating step.

Example 3

Crude maleic anhydride recovered by distillation from an organic absorbent (1609 g) was mixed with 6.46 g (0.4%) of $P_2O_5$ and 3.22 g (0.2%) of magnesium chloride. This mixture was charged to a 20-sieve-tray column and heated at total reflux under a pressure of 51 torr for 1 hour. After this time, distillation was carried out to give five fractions, which were each tested in the 24-hour color thermal stability test. The results were as follows:

| Cut No. | Weight, grams | Color (Hazen) after test |
| --- | --- | --- |
| 1 | 99.5 | 200 |
| 2 | 98.5 | 40 |
| 3 | 98.5 | 35 |
| 4 | 970.0 | 25 |
| 5 | 98.9 | 40 |

This example shows that satisfactory product was obtained from simultaneous treatment during distillation; thus, the present invention contemplates that the treatment "before" distillation to obtain product distilled anhydride includes treatment during distillation but before the product is withdrawn as an overhead stream.

Example 4

Crude maleic anhydride obtained as before (1862 G) was charged to a 20-sieve-tray column. One fraction (67 g) was taken overhead at a pressure of 100 torr and a 9:1 reflux ratio. Then 1777 g of the bottoms from this distillation was mixed with 27 g (1.5%) $P_2O_5$, heated and stirred under a nitrogen blanket at 310°F. for 6 hours. At the end of this treatment, the mixture was filtered. The filtrate, 1536 g, was distilled in a 20-sieve-tray column as before. The various fractions were tested for thermal color stability at 140°C. for 24 hours. The results were as follows:

| Cut No. | Weight, grams | Color (Hazen) after test |
|---|---|---|
| 1 | 106.5 | 100 |
| 2–6 | 1285.6 | >500* |
| 7 | 80.1 | >500 |

*each of cuts 2 through 6 was over 500 Hazen

This experiment illustrates that even a massive dosage of $P_2O_5$ alone was not sufficient to give a thermally color stable product.

Example 5 a. Crude maleic anhydride was obtained by distillation from an organic absorbent. A portion of this material (5079 g) was mixed with 10.2 g (0.2%) $P_2O_5$ and 5.1 g (0.1%) magnesium chloride and heated for 1 hour at 265°F. It was then distilled dto give a 2.5 weight percent forecut, an 85% product cut, and the remainder was left as bottoms.

b. A portion of crude maleic anhydride was distilled without treatment to give a 2.5% forecut and an 85% product cut.

c. A portion of crude maleic anhydride was treated with 0.2% $P_2O_5$ only, and then distilled as before.

d. A portion of crude maleic anhydride was treated with 0.1% magnesium chloride only, and then distilled as before.

All forecuts and product cuts of the above four distillations were tested for long-term color thermal stability by the test previously described. The results were as follows:

| Treatment | Color (Hazen) after test | |
|---|---|---|
| | Forecut | Product cut |
| a) $P_2O_5$ & $MgCl_2$ | 275 | 45 |
| b) None | >>500 | >>500 |
| c) $P_2O_5$ only | >500 | 360 |
| d) $MgCl_2$ only | >500 | 400 |

All of the above product cut fractions were of high purity maleic anhydride, having melting points in excess of 52.5°C. This example illustrates that although either $P_2O_5$ or $MgCl_2$ alone effect some improvement in color thermal stability, a high-quality product is only obtained by treating with both agents.

Example 6

Crude maleic anhydride obtained by distilling from an organic absorbent was charged to a distilling column, and a fraction (5%) of the charge was taken overhead. Then 1585 g of the bottoms was mixed with 3.4 g (0.2%) $P_2O_5$ and 1.7 g (0.1%) vanadium trichloride. The resulting mixture was stirred and heated at 300°F. for 1 hour. It was then distilled at a pressure of 50 torr. The product fraction, 64.5 weight percent of the charge, had a Hazen color of 55 after heating at 140°C. for 24 hours.

Example 7

This example was carried out essentially the same as Example 6, except that 1607 g of topped crude maleic anhydride was treated with 3.2 g (0.2%) $P_2O_5$ and 2.6 g (0.1%) ferric chloride hexahydrate. Distillation gave a 21% forecut, a 52% product cut and a 15% aftercut. The 24-hour color thermal stability values were 25, 15 and 45 respectively, i.e., all of the distilled maleic anhydride was of satisfactory quality.

Example 8

Crude maleic anhydride recovered from an organic absorbent was redistilled and a center-cut portion (1200 g) was mixed with 6.0 g (0.5%) $P_2O_5$ and 6.0 g (0.5%) manganous chloride tetrahydrate. This mixture was charged to a distillation pot and distilled through a 20-sieve-tray column under a pressure of 57 torr. A forecut (70.0 g) and five product cuts totaling 1071 g (89.5%) were obtained. The product cuts had Hazen colors ranging from 20 to 60 (weight average 35) after the thermal stability test (24 hours at 140°C.). The untreated stock had a Hazen color greatly in excess of 500 after the same test.

Example 9 a. Crude maleic anhydride obtained from an organic absorbent (1200 g) was mixed with 6.0 g (0.5%) calcium chloride and 2.4 g(0.2%) sodium perborate tetrahydrate. This mixture was then distilled in a 20-sieve-tray column at a pressure of 57 torr. A forecut (56 g) and five product cuts (1091 g), 91% of charge, were obtained. The product cuts had colors ranging from 90 to 175 Hazen (weight average 100) after heating for 24 hours at 140°C. The untreated starting material had a final color greater than 500 Hazen after the same test.

b. The same crude maleic anhydride (1400 g) was mixed with 2.8 g (0.2%) of sodium perborate tetrahydrate and distilled as in Example 9(a). The product cuts (1257 g, 90% of charge) all had color thermal stability values in excess of 500 Hazen.

c. The same crude maleic anhydride (1400 g) was mixed with 7.0 g (0.5%) calcium chloride and distilled as before. The product cuts (1271 g, 86% of charge) had color thermal stability values ranging from 140 to 250 Hazen (weight average 185).

d. Example 9(a) was repeated using a different stock of crude maleic anhydride, but this stock was produced in the same general way as with the stock used in Example 9(a). In this case, the product cuts had color thermal stability values of 15 to 90 (average 20).

This example shows that sodium perborate plus calcium chloride treatment gives a considerably improved product over that obtained by using either of the two agents alone.

Example 10

Another sample of crude maleic anhydride (1400 g) obtained from an organic absorbent was mixed with 2.8 g (0.2%) $P_2O_5$ and 2.8 g (0.2%) calcium chloride and distilled as in Example 9. The product cuts (1258 g, 90% of charge) had color thermal stability values ranging from 20 to 100 Hazen (weight average 25).

Example 11

Crude maleic anhydride obtained as in Example 1 was used for a series of treating tests with various treating agents. In these tests, 40 g of crude maleic anhydride was mixed with the indicated amount of agent. Each mixture was then sealed under vacuum in 80 ml Carius tubes. After about 1 to 3 hours at the indicated temperature, each sample tube was distilled at 150 torr. The treated and distilled samples were then heated at 140°C. for 24 hours. The treating conditions and results are as follows:

TABLE I

| Agent | Quantity (grams) | Temperature of Treating °F. |
|---|---|---|
| Activated carbon | 1.2 | 150 |
| Clay | 2.0 | 150 |
| Alumina | 2.0 | 150 |
| Chromium oxide | 0.4 | 300 |
| Ferric oxide | 0.4 | 300 |
| Calcium oxide | 0.4 | 300 |
| Lead oxide | 0.4 | 300 |
| Palladium oxide on carbon | 0.4 | 300 |
| Boric acid | 0.4 | 300 |
| Boric anhydride | 0.4 | 300 |
| Ammonium sulfate | 0.2 | 300 |
| Sodium sulfate | 0.2 | 300 |
| Ammonium hydrogen phosphate | 0.8 | 250 |
| t-Butyl peroxide | 0.2 | 100 to 300 |
| Benzoyl peroxide | 0.4 | 100 to 300 |

In all cases, the distilled product had a color thermal stability value in excess of 500 Hazen. The numerous examples indicated in Table I are from a part of our research work prior to the examples, such as Example 1, illustrating the present invention.

What is claimed is:

1. In a process for obtaining purified maleic anhydride from crude maleic anhydride wherein the maleic anhydride is produced by steps comprising oxidizing a hydrocarbon feedstock over a catalyst comprising vanadium and phosphorus oxides to obtain an effluent gas containing maleic anhydride, and recovering the crude maleic anhydride from the effluent gas by contacting the effluent gas with an organic absorbent followed by stripping the crude maleic anhydride out of the absorbent, and wherein the crude maleic anhydride is treated by steps comprising heating the crude maleic anhydride, distilling the crude maleic anhydride, and withdrawing a purified maleic anhydride overhead product, the improvement which comprises combining, contacting and heating an alkaline earth or transition metal chloride and $P_2O_5$ or alkali or alkaline earth metal perborate with the crude anhydride before distilling the crude anhydride to obtain overhead produce maleic anhydride.

2. A process in accordance with claim 1 wherein the metal chloride is Mg, Ca, Sr, Ba, Mn, or Fe chloride.

3. A process in accordance with claim 1 wherein the perborate is sodium perborate.

4. A process in accordance with claim 2 wherein the metal chloride is Mg, Ca, Mn, or Fe chloride and the amount of the metal chloride combined with the crude maleic anhydride is between 0.01 and 2 weight percent of the maleic anhydride.

5. A process in accordance with claim 4 wherein the metal chloride is Mg chloride.

6. A process in accordance with claim 4 wherein the metal chloride is Fe chloride.

7. A process in accordance with claim 4 wherein the metal chloride is Ca chloride.

8. A process for obtaining purified maleic anhydride from crude maleic anhydride produced by steps comprising oxidizing butane over a solid catalyst comprising vanadium and phosphorus oxides to obtain a gaseous effluent containing maleic anhydride, contacting the gaseous effluent with an organic absorbent thereby absorbing maleic anhydride and obtaining a maleic-anhydride-rich absorbent, stripping maleic anhydride from the rich absorbent to obtain crude maleic anhydride, which process comprises a. combining and contacting 0.05 to 2 weight percent Mg, Ca, Mn, or Fe chloride and 0.05 to 2 weight percent $P_2O_5$ or $NaBO_3$ with the crude maleic anhydride to obtain a mixture, b. holding the mixture at a temperature between about 150° and 350°F. for between 0.1 and 12 hours, and c. distilling the mixture to obtain a purified overhead maleic anhydride fraction.

9. A process in accordance with claim 8 wherein the treating agents of step (a) are 0.05 to 2 weight percent Mg, Ca, Mn, or Fe chloride and 0.05 to 2 weight percent $P_2O_5$.

* * * * *